(12) United States Patent
Bontus et al.

(10) Patent No.: US 7,548,603 B2
(45) Date of Patent: Jun. 16, 2009

(54) METHOD AND APPARATUS FOR EXACT CONE BEAM COMPUTED TOMOGRAPHY

(75) Inventors: Claas Bontus, Hamburg (DE); Thomas Köhler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 407 days.

(21) Appl. No.: 10/534,158

(22) PCT Filed: Nov. 3, 2003

(86) PCT No.: PCT/IB03/04952

§ 371 (c)(1),
(2), (4) Date: May 5, 2005

(87) PCT Pub. No.: WO2004/044849

PCT Pub. Date: May 27, 2004

(65) Prior Publication Data

US 2006/0039525 A1    Feb. 23, 2006

(30) Foreign Application Priority Data

Nov. 11, 2002   (DE)   ................. 102 52 661

(51) Int. Cl.
*A61B 6/03* (2006.01)
(52) U.S. Cl. ............... 378/4; 378/15; 378/901
(58) Field of Classification Search ........ 378/4, 378/15, 901, 210; 382/131
See application file for complete search history.

(56) References Cited

U.S. PATENT DOCUMENTS

| | | | |
|---|---|---|---|
| 4,570,224 A * | 2/1986 | Shimoni et al. ........... 378/13 |
| 4,636,952 A | 1/1987 | Crawford | |
| 4,703,424 A | 10/1987 | Gullberg et al. | |
| 5,341,460 A | 8/1994 | Tam | |
| 5,404,293 A * | 4/1995 | Weng et al. ............... 378/15 |
| 5,559,335 A * | 9/1996 | Zeng et al. ............ 250/363.04 |
| 5,708,690 A | 1/1998 | Hsieh | |
| 5,764,720 A | 6/1998 | Besson | |
| 6,075,836 A * | 6/2000 | Ning .................... 378/98.12 |
| 6,104,775 A * | 8/2000 | Tuy ........................ 378/4 |
| 6,285,733 B1 * | 9/2001 | Proksa et al. ............. 378/15 |
| 6,529,575 B1 * | 3/2003 | Hsieh ....................... 378/4 |

(Continued)

FOREIGN PATENT DOCUMENTS

DE    19944701 A1 *    3/2001

OTHER PUBLICATIONS

Turbell et al., An improved PI-method for reconstruction for helical cone-beam projections, Oct. 24-30, 1999, Nuclear Science Symposium, 1999, IEEE, pp. 865-868.*

(Continued)

*Primary Examiner*—Edward J Glick
*Assistant Examiner*—John M Corbett (57) ABSTRACT

The invention relates to a computed tomography method in which an examination zone is irradiated along a helical trajectory by a conical radiation beam. The radiation transmitted by the examination zone is measured by means of a detector unit and therefrom the absorption distribution in the examination zone is reconstructed without approximations. The reconstruction comprises a derivation of the measuring values of parallel rays of different projections, an integration of these values along K lines, a weighting of these values and a back projection.

16 Claims, 6 Drawing Sheets

U.S. PATENT DOCUMENTS

| | | | |
|---|---|---|---|
| 6,574,299 B1* | 6/2003 | Katsevich | 378/15 |
| 6,778,629 B1* | 8/2004 | Danielsson et al. | 378/15 |
| 2004/0062341 A1* | 4/2004 | Popescu et al. | 378/4 |

OTHER PUBLICATIONS

Turbell, Cone-Beam Reconstruction Using Filtered Backprojection, Feb. 2001, Linkoping Studies in Science and Technology Dissertation No. 672, ISBN 91-7219-919-9.*

Katsevich, Analysis of an exact inversion algorithm for spiral cone-beam CT, Aug. 7, 2002, Phys. Med. Biol., vol. 42, pp. 2583-2597.*

Turbell et al., The PI-Method: Non-Redundant Data Capture and Efficient Reconstruction for Helical Cone-Beam CT, 1999, IEEE, pp. 1424-1425.*

Proksa et al., The n-PI-Method for Helical Cone-Beam CT, 2000, IEEE Transactions on Medical Imaging, vol. 19, No. 9, pp. 848-863.*

Kohler et al., Evaluation of Helical Cone-Beam CT Reconstruction Algorithms, Nov. 10-16, 2002, IEEE Nuclear Science Symposium Conference Record 2002, pp. 1217-1220.*

Tuy, 3D Image Reconstruction for Helical Partial Cone Beam Scanners, 1999, Proceedings of the 1999 International Meeting on Fully Three-Dimensional Image Reconstruction in Radiology and Nuclear Medicine, pp. 7-10.*

Weisstein, CRC Concise Encyclopedia of Mathematics, second edition, 2003, pp. 382-383 and 1566-1567.*

Katsevich, A.; Analysis of an exact inversion algorithm for spiral cone-beam CT; Physics in Med. & Bio.; 2002; 47:2583-2597.

Katsevich, A.; Theoretically Exact Filtered Backprojection-type Inversion Algorithm for Spiral CT; SIAM J. Appl. Math; 2002; 62:2012-2026.

Kohler, TH., et al.; Evaluation of Helical Cone-Beam CT Reconstruction Algorithms; IEEE; 2003; 1217-1220.

Kohler, TH., et al.; Artifact analysis of approximate helical cone-beam CT reconstruction algorithms; Med. Phys; 2002; 29:51-64.

* cited by examiner

METHOD AND APPARATUS FOR EXACT CONE BEAM COMPUTED TOMOGRAPHY

The invention relates to a computed tomography method in which an examination zone is irradiated along a helical trajectory by a conical X-ray beam. Moreover, the invention relates to a computer tomograph as well as to a computer program for controlling the computer tomograph.

In known methods of the kind set forth, utilizing approximations, the variation in space of the absorption or the attenuation of the radiation in the examination zone can be reconstructed from the measuring values acquired by a detector unit. Such approximations, however, give rise to artifacts in the reconstructed images, said artifacts being more pronounced as the angle of aperture of the radiation beam is larger in the direction of the axis of rotation ("Artifact Analysis of Approximative Cone-Beam CT Algorithms, Medical Physics, Vol. 29, pp. 51-64, 2002).

Known exact methods are usually based on Radon inversion. They require a large amount of calculation work and give rise to discretization errors in the reconstructed images.

Moreover, an exact method which utilizes filtered back projection is known from "Analysis of an Exact Inversion Algorithm for Spiral Cone-Beam CT", Physics Medicine and Biology, Vol. 47, pp. 2583-2597 (E1). This method again requires a large amount of calculation work, thus giving rise to long reconstruction times.

Therefore, it is an object of the present invention to provide a method which enables faster, exact reconstruction of the absorption distribution in the examination zone.

In respect of the method this object is achieved by means of a computed tomography method which comprises the steps of:

generating, using a radiation source, a conical radiation beam which traverses an examination zone or an object present therein, generating a relative motion between the radiation source on the one side and the examination zone or the object on the other side, which relative motion comprises a rotation about an axis of rotation and a displacement parallel to the axis of rotation and is shaped as a helix, acquiring measuring values which are dependent on the intensity in the radiation beam on the other side of the examination zone by means of a detector unit during the relative motions, reconstructing a CT image of the examination zone from the measuring values, in which reconstruction an exact 3D back projection comprising the following steps is carried out:

determining the partial derivative of measuring values of parallel rays with different radiation source positions in conformity with the angular position of the radiation source, weighted integration of the derived measuring values along K lines, multiplying all measuring values by a weighting factor which corresponds to the cosine of the cone angle of the beam associated with the relevant measuring value, multiplying all measuring values by a weighting factor which corresponds to the reciprocal value of the cosine of the fan angle of the beam associated with the relevant measuring value, reconstructing the absorption of each object point by back projection of the measuring values.

In conformity with the method which is known from E1, prior to the back projection the measuring values must be multiplied by weighting factors which are dependent on the location of the object point to be reconstructed in the examination zone. In contrast therewith, in accordance with the invention the measuring values are multiplied by weighting factors prior to the back projection, said weighting factors being dependent on the location of the measuring value on the detector unit. Because the number of object points to be reconstructed generally is much smaller than the number of detector elements, exact reconstruction is thus possible while requiring a comparatively small amount of calculation work only. Moreover, as opposed to the method which is known from E1, the integration interval in the back projection in accordance with the invention is not dependent on the object point, so that it is not necessary to determine an integration interval for each object point during the back projection, thus leading to a further reduction of the amount of calculation work required.

Claim 2 describes a preferred reconstruction method which involves an amount of calculation work which is smaller in comparison with other methods and which leads to a favorable image quality.

Claim 3 discloses a preferred version of the integration via a K line, notably the multiplication by means of a weighting factor which leads to a high image quality.

A computer tomograph for carrying out the method is disclosed in claim 4. Claim 5 defines a computer program for controlling a computer tomograph as claimed in claim 4.

The invention will be described in detail hereinafter with reference to the drawings. Therein

Figure 1:
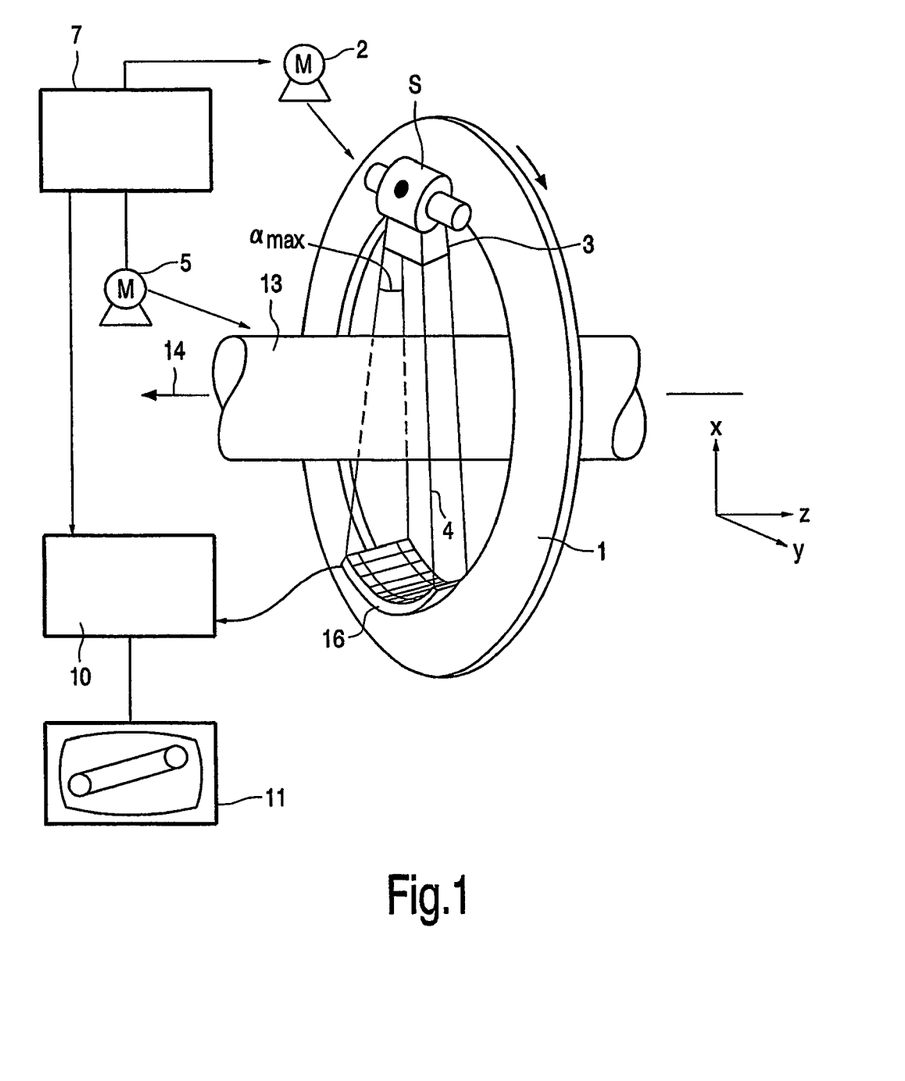
FIG. 1 shows a computer tomograph which is suitable for carrying out the method in accordance with the invention.

The computer tomograph shown in FIG. 1 comprises a gantry 1 which is capable of rotation about an axis of rotation 14 which extends parallel to the z direction of the co-ordinate system shown in FIG. 1. To this end, the gantry 1 is driven by a motor 2 at a preferably constant, but adjustable angular speed. A radiation source S, for example, an X-ray source, is mounted on the gantry 1. The radiation source is provided with a collimator arrangement 3 which forms a conical radiation beam 4 from the radiation generated by the radiation source S, that is, a radiation beam which has a finite dimension other than zero in the z direction as well as in a direction perpendicular thereto (that is, in a plane perpendicular to the axis of rotation).

The radiation beam 4 traverses a cylindrical examination zone 13 in which an object, for example, a patient on a patient table (both not shown) or also a technical object may be situated. After having traversed the examination zone 13, the radiation beam 4 is incident on a detector unit 16 which is attached to the gantry 1 and comprises a detector surface which comprises a plurality of detector elements arranged in rows and columns in the form of a matrix in the present embodiment. The detector columns extend parallel to the axis of rotation 14. The detector rows are situated in planes which extend perpendicularly to the axis of rotation, that is, preferably on an arc of a circle around the radiation source S. However, they may also have a different shape, for example, an arc of a circle around the axis of rotation 14 or be rectilinear. Generally speaking, the detector rows comprise more detector elements (for example, 1000) than the detector columns (for example, 16). Each detector element struck by the radiation beam 4 produces a measuring value for a ray of the radiation beam 4 in each position of the radiation source.

The angle of aperture of the radiation beam 4, denoted by the reference $\alpha_{max}$, determines the diameter of the object cylinder within which the object to be examined is situated during the acquisition of the measuring values. The angle of aperture is defined as the angle enclosed by a ray situated at the edge of the radiation beam 4 in a plane perpendicular to the axis of rotation with respect to a plane defined by the radiation source S and the axis of rotation 14. The examination zone 13, or the object or the patient table, can be displaced parallel to the axis of rotation 14 or to the z axis by means of a motor 5. As an equivalent, however, the gantry could also be displaced in this direction.

When a technical object is concerned instead of a patient, the object can be rotated during an examination while the radiation source S and the detector unit 16 remain stationary.

When the motors 2 and 5 operate simultaneously, the radiation source S and the detector unit 16 describe a helical trajectory relative to the examination zone 13. However, when the motor 5 for the displacement in the direction of the axis of rotation 14 is stationary and the motor 2 rotates the gantry, a circular trajectory is obtained for the radiation source and the detector unit 16 relative to the examination zone 13. Hereinafter only the helical trajectory will be considered.

The measuring values acquired by the detector unit 16 are applied to an image processing computer 10 which is connected to the detector unit 16, for example, via a wireless data transmission (not shown). The image processing computer 10 reconstructs the absorption distribution in the examination zone 13 and reproduces it, for example, on a monitor 11. The two motors 2 and 5, the image processing computer 10, the radiation source S and the transfer of the measuring values from the detector unit 16 to the image processing computer 10 are controlled by a control unit 7.

In other embodiments the acquired measuring values can first be applied to one or more reconstruction computers for reconstruction, said computers applying the reconstructed data to the image processing computer, for example, via an optical fiber cable.

Figure 2:
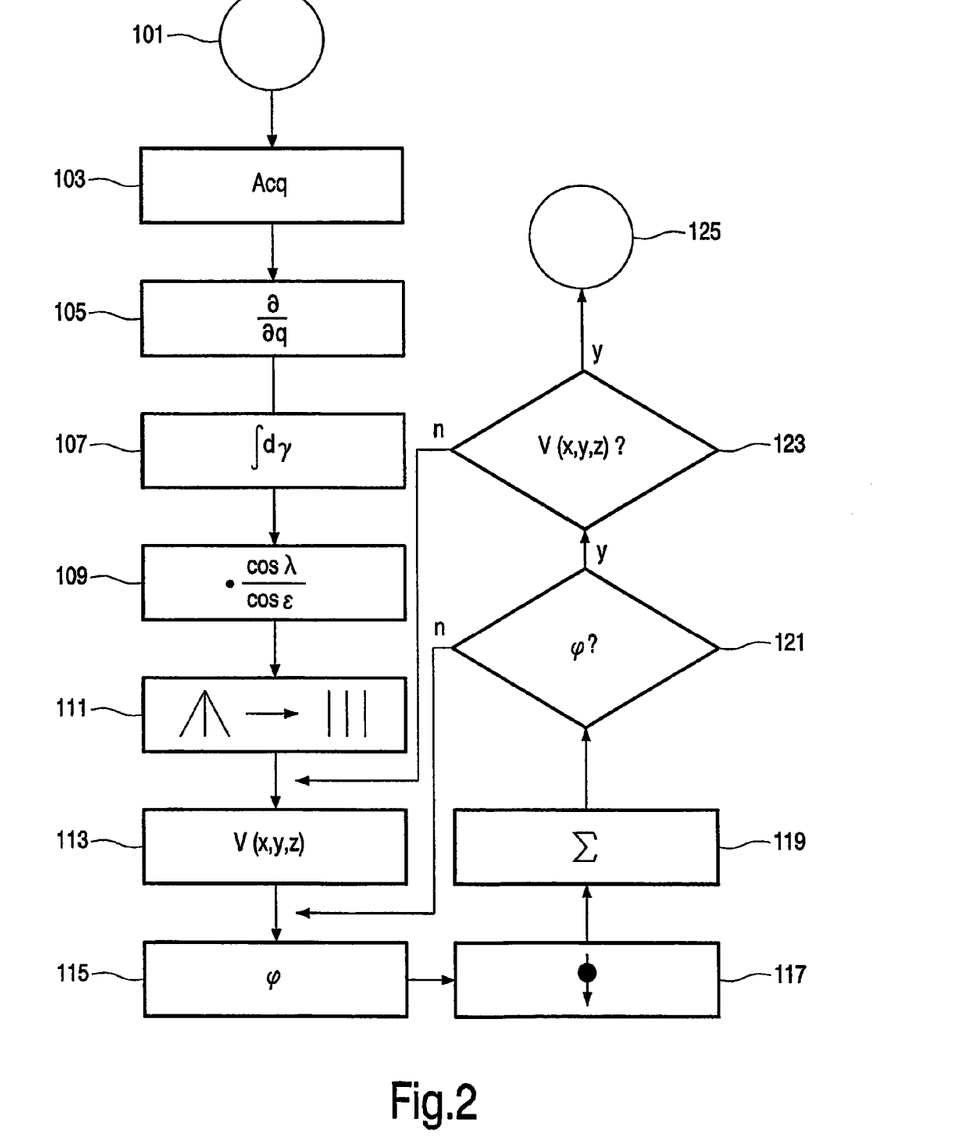
FIG. 2 shows a flow chart of the method in accordance with the invention.

FIG. 2 shows a flow chart illustrating a version of a measuring and reconstruction method that can be executed by means of the computer tomograph shown in FIG. 1.

After the initialization in the step 101, the gantry rotates at an angular speed which is constant in the present embodiment. However, it may also vary, for example, in dependence on the time or on the radiation source position. In the step 103 the examination zone, or the object or the patient table, is displaced parallel to the axis of rotation and the radiation of the radiation source S is switched on, so that the detector unit 16 can detect the radiation from a plurality of angular positions.

In order to understand the next steps, reference is made to the following equation from "Analysis of an Exact Inversion Algorithm for Spiral Cone-Beam CT", Physics Medicine and Biology, Vol. 47, pp. 2583-2597:

$$f(x) = -\frac{1}{2\pi^2} \int_{I_{PI(x)}} ds \frac{1}{|x-y(s)|} \int_{-\pi}^{\pi} \frac{d\gamma}{d\sin\gamma} \frac{\partial}{\partial q} D_f(y(q), \Theta(s, x, \gamma))|_{q=s}. \quad (1)$$

This equation describes an exact reconstruction of the absorption by back projection of the measuring values. Therein, f(x) denotes the spatial absorption distribution in the examination zone in the location x and $I_{PI}(x)$ describes the part of the helix which is enclosed by a PI line 31.

Figure 3:
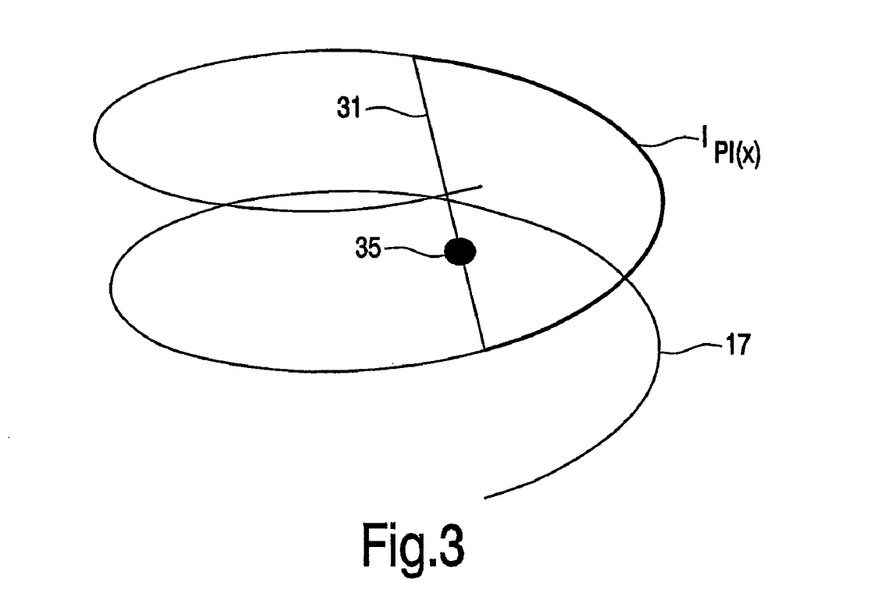
FIG. 3 shows a PI line and a path of integration for a point in the examination zone.
Figure 4:
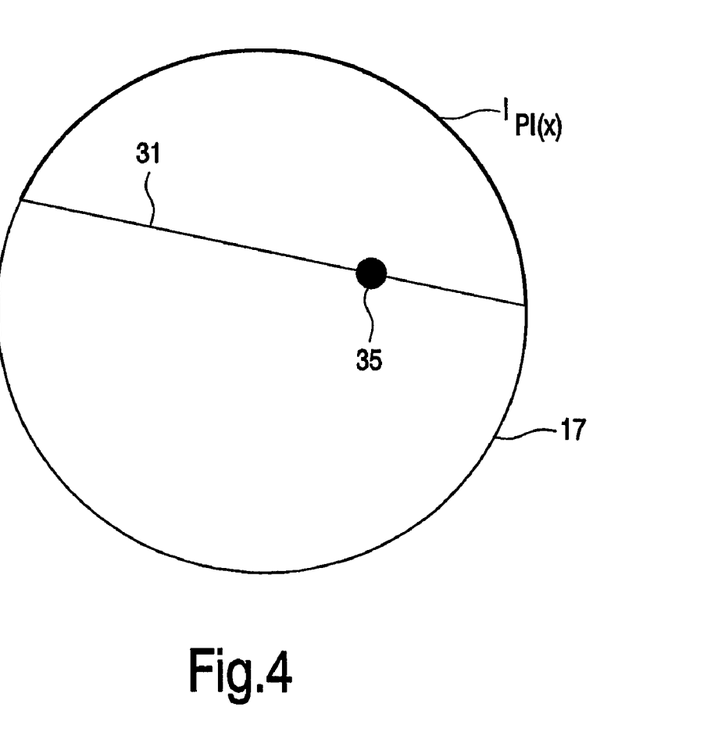
FIG. 4 shows the PI line and the path of integration for a point in the examination zone projected in a plane perpendicular to the axis of rotation.

The PI line 31 of an object point 35 in the location x in the examination zone and $I_{PI(x)}$ are shown in FIG. 3 and FIG. 4 and will be described in detail hereinafter. The radiation source moves relative to the examination zone around an object point 35 on a helical path 17. The PI line 31 then is the line which intersects the helix in two locations and the object point 35, the helical segment $I_{PI}(x)$ enclosed by the line then covering an angle smaller than $2\pi$.

Furthermore, in the equation (1) the reference s is the angular position of the radiation source S on the helix related to an arbitrary but fixed reference angular position and the reference y(s) is the position of the radiation source in three-dimensional space.

The measuring value $D_f(y,\Theta)$ can be described by the following line integral $$D_f(y(q), \Theta) = \int_0^\infty dl f(y + l\Theta). \quad (2)$$

The unity factor $\Theta$ therein indicates the direction of the ray associated with the measuring value.

Figure 5:
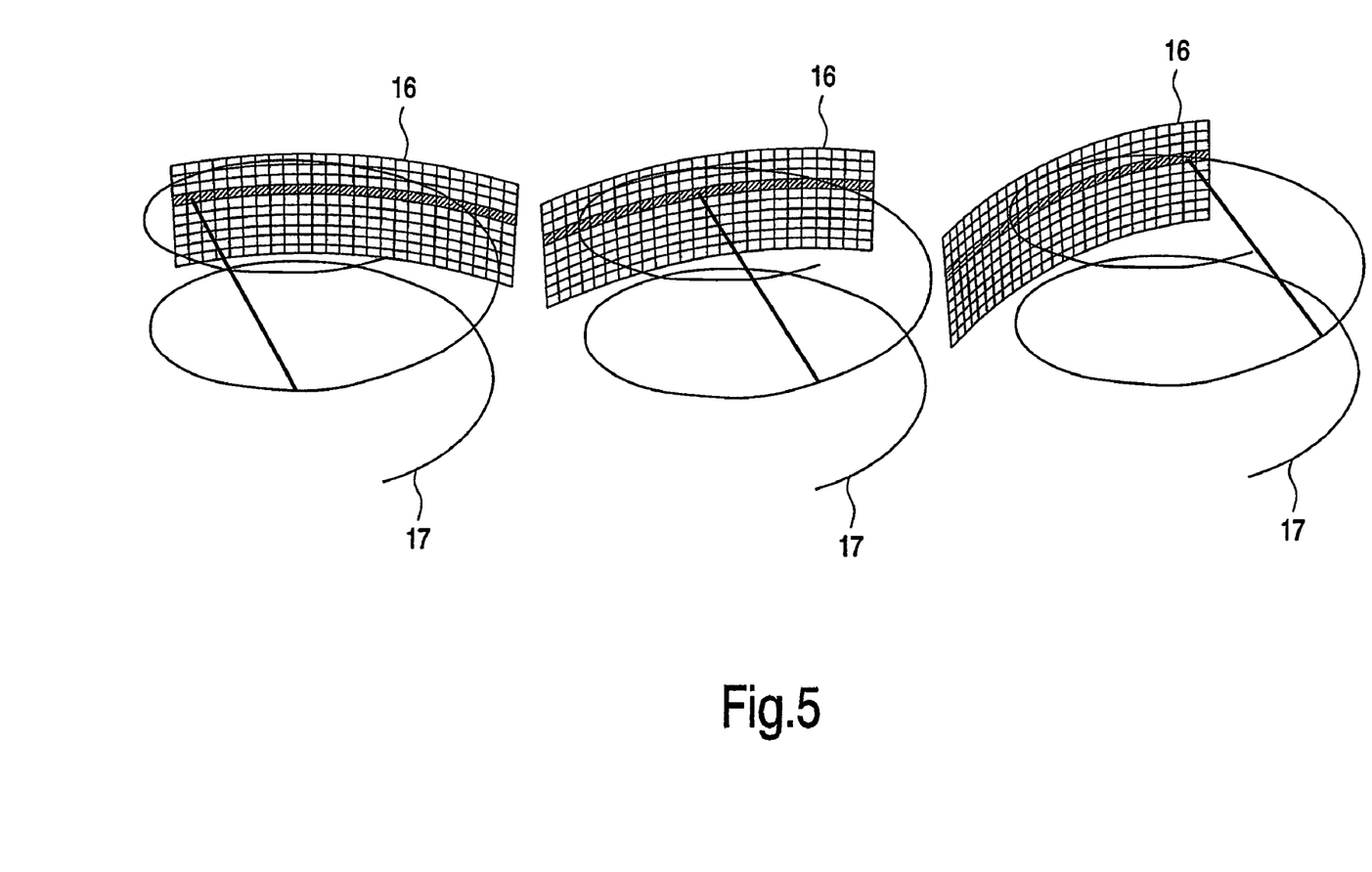
FIG. 5 shows parallel beams with different beam positions.

In the step 105 in conformity with equation (1) the measuring values are partially derived according to q, that is, in conformity with the angular position of the radiation source in the location q=s. In this respect it is to be noted that only y is dependent on q and not $\Theta$, so that measuring values of parallel rays have to be taken into account for the derivation. Parallel rays have the same cone angle, the cone angle of a ray being the angle enclosed by the projection of the ray in the xz plane of the co-ordinate system shown in FIG. 1 relative to the ray which extends through the axis of rotation and perpendicular thereto. As is shown in FIG. 5, rays having the same cone angle are incident on the same detector row in the case of a focus-centered detector, so that for the partial derivation measuring values of the same row but from different projections are taken into account. The derivation can then take place, for example, by means of the finite difference method.

Figure 6:
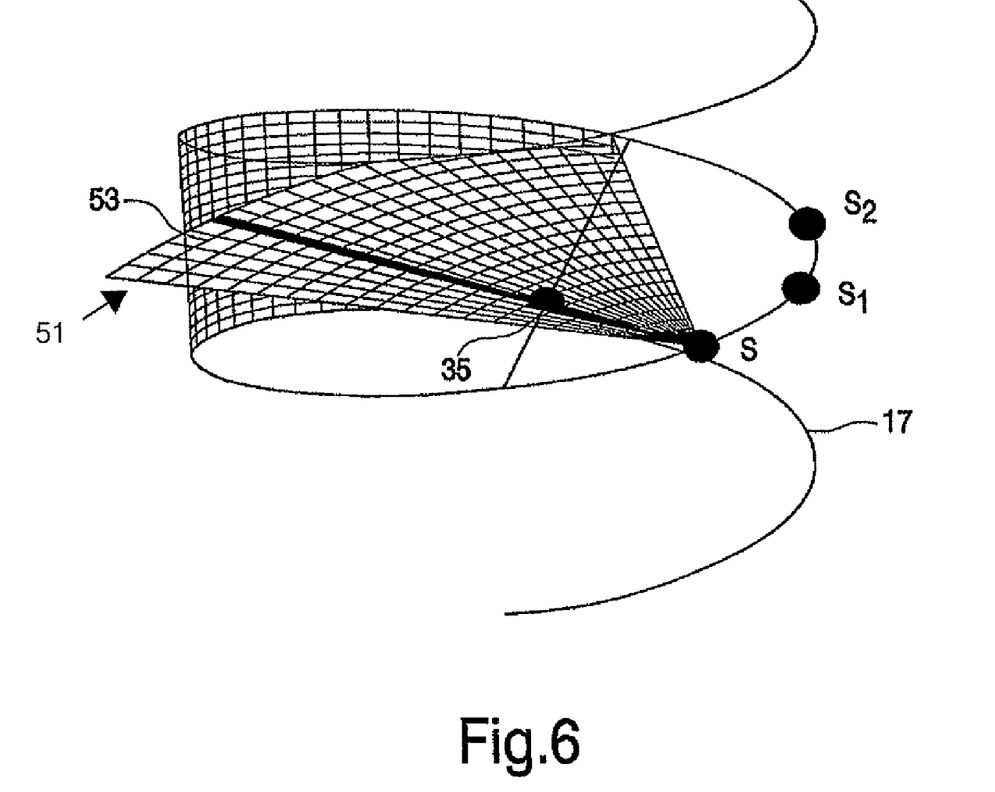
FIG. 6 shows a K plane and a K line.

The unity factor $\Theta$ is dependent on the K angle $\gamma$ which can be described by means of the so-called K planes 51. The K planes 51 will be described in detail hereinafter.

In order to determine a K plane 51 a function $$s_1(s, s_2) = \begin{cases} \dfrac{ms_2 + (n-m)s}{n}, & s \leq s_2 < s + 2\pi \\ \dfrac{ms + (n-m)s_2}{n}, & s > s_2 > s - 2\pi \end{cases} \quad (3)$$

is introduced, which function is dependent on non-negative, integer values n and m, where n>m. In this embodiment n=2 and m=1. However, other values n, m may also be chosen. The equation (1) would nevertheless remain exact, and only the position of the K planes 51 would change. Furthermore, the vector function $$u(s, s_2) = \begin{cases} \frac{[y(s_1(s, s_2)) - y(s)] \times [y(s_2) - y(s)]}{|[y(s_1(s, s_2)) - y(s)] \times [y(s_2) - y(s)]|} \cdot \text{sgn}(s_2 - s), & 0 < |s_2 - s| < 2\pi \\ \frac{\dot{y}(s) \times \ddot{y}(s)}{|\dot{y}(s) \times \ddot{y}(s)|}, & s_2 = s \end{cases} \quad (4)$$

and the unity vector $$\beta(s, x) = \frac{x - y(s)}{|x - y(s)|} \quad (5)$$

are defined. The vector β then points from the radiation source position y(s) to the position x. In order to determine the K plane, a value $s_2 \in I_{PI(x)}$ is chosen so that y(s), $y(s_1(s,s_2))$, $y(s_2)$ and x are situated in one plane. This plane is referred to as the K plane 51 and the line of intersection between the K plane 51 and the detector surface is referred to as the K line 53. FIG. 6 shows a fan-like part of a K plane. The edges of the fan meet at the location of the radiation source. This definition of the K plane 51 is equivalent to solution of the equation $$(x - y(s)) \cdot u(s, s_2) = 0, \quad s_2 \in I_{PI(x)} \quad (6)$$

according to $s_2$. Thus, u is thus the normal vector of the K plane 51. In order to determine the vector function $\Theta(s,x,y)$ the vector $$e(s,x) = \cos \gamma \cdot \beta(s,x) + \sin \gamma \cdot e(s,x) \quad (7)$$

is defined. Using the definition for β and e, the vector function $\Theta(s,x,y)$ can be expressed as follows:

$$\Theta(s,x,\gamma) = \cos \gamma \cdot \beta(s,x) + \sin \gamma \cdot e(s,x) \quad (8)$$

Because both vectors β and e are oriented perpendicularly to u, the K angle γ indicates the direction of the vector Θ and hence the direction of a ray within a K plane.

The K planes and K lines are described in detail in E1 which is explicitly referred to herein.

In the step 107 the measuring values derived along K lines are multiplied by a weighting factor, corresponding to the inverse sine of the K angle γ, and integrated in conformity with the equation (1). To this end, for each location x in the examination zone and for each projection angle there is determined a K line; as described above, a value $s_2 \in I_{PI(x)}$ is then chosen to be such that y(s), $y(s_1(s,s_2))$, $y(s_2)$ and x are situated in one plane, that is, the K plane. The K line is then determined as the line of intersection between the K plane and the detector surface. The multiplications by the weighting factor and the integrations can be performed, for example, by means of Fourier filtering.

The derived and integrated measuring values can be represented by the following equation:

$$p(y(s), \phi(s, x)) = \int_{-\Pi}^{\Pi} \frac{d\gamma}{\sin\gamma} \frac{\partial}{\partial q} D_f(y(q), \Theta(s, x, \gamma))|_{q=s}. \quad (9)$$

Therein, $p(y(s),\Phi(s,x))$ denote the derived and integrated measuring values and $\Phi(s,x)$ is a unity factor which points from the radiation source position y(s) in the direction of the location x in the examination zone.

The missing integration step in the equation (1) or the back projection of the measuring values can now be described by the following equation:

$$f(x) = -\frac{1}{2\pi^2} \int_{I_{PI(x)}} ds \frac{1}{|x - y(s)|} p(y(s), \Phi(s, x)). \quad (10)$$

In conformity with this equation each measuring value must be multiplied by the factor $1/|x-y(s)|$ in order to reconstruct the spatial absorption distribution in the examination zone. This factor is dependent on the location x, so that it must be calculated anew for each combination of the radiation source position y(s) and the location x. Moreover, the integration over s takes place along the segment of the helix $I_{PI(x)}$. Thus, the integration interval is dependent on the location x in which the absorption is to be determined, so that the integration interval must be determined for each location x. Because the integration in conformity with the equation (10) would require a large amount of calculation work for these reasons, the integration variable s is replaced by the projection angle φ hereinafter. The projection angle φ is then the angle enclosed by the PI line of the object point x projected in a plane perpendicular to the axis of rotation (referred to hereinafter as the xy plane) and the projection on the xy plane of the ray which passes through the location x while emanating from the radiation source.

The integration in the equation (10) is carried out along the helical segment $I_{PI(x)}$. This segment is enclosed by the PI line, so that an integration must be performed for each measuring value from 0 to π after substitution of the integration variables. Thus, the integration interval is the same for each location x in the examination zone.

Figure 7:
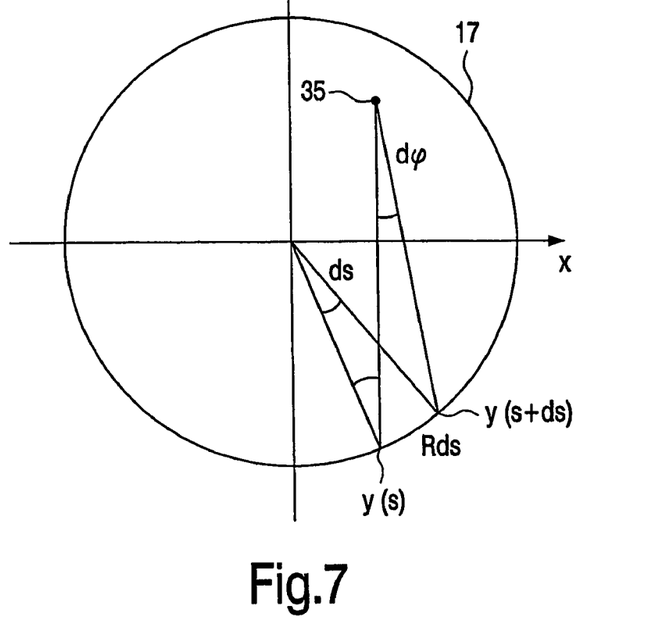
FIG. 7 is a diagrammatic view of two different radiation source positions of the radiation source, a point in the examination zone and the trajectory projected in a plane perpendicular to the axis of rotation.

The relationship between the integration variables ds and dφ can be derived from FIG. 7. This Figure shows a projection of a helix 17, the object point 35 in the location x and the radiation source positions y(s) and y(s+ds) on the xy plane. The following equation results from FIG. 7:

$$d\varphi = \frac{|P_{xy}(y)| ds \cos \varepsilon}{|P_{xy}(x-y)|} = \frac{Rds \cos \varepsilon}{\sqrt{(x_x - y_x)^2 + (x_y - y_y)^2}}. \quad (11)$$

Therein, $P_{xy}$ denotes the projection operator for the projection of a vector in the xy plane and R denotes the radius of the helix 17. The fan angle ε is the angle enclosed by the normal from the radiation source position to the axis of rotation and the projection of the ray which emanates from the radiation source position and passes through the location x on the xy plane. The indices x and y describe x and y components of a vector. The components relate to the cartesian co-ordinate system shown in FIG. 1.

Thus, the following equation can be derived for the cone angle λ:

$$\cos\lambda = \frac{\sqrt{(x_x - y_x)^2 + (x_y - y_y)^2}}{|x - y|}. \quad (12)$$

The equations (10), (11) and (12) yield $$f(x) = -\frac{1}{2\pi^2}\int_0^\pi d\varphi \frac{\cos\lambda}{R\cos\varepsilon} p(y(s(\varphi)), \Phi(s(\varphi), x)). \quad (13)$$

In conformity with this equation, in the step 109 the measuring values are multiplied by a first weighting factor, corresponding to the cosine of the cone angle $\lambda$, and by a second weighting factor which corresponds to the reciprocal value of the cosine of the fan angle $\epsilon$. Moreover, the measuring values can be multiplied by the inverse radius R. Because the radius is constant during the acquisition, the latter multiplication can also be performed after the back projection.

For small angles $\lambda$ and $\epsilon$, the multiplication by the weighting factors $\cos(\lambda)$ and $1/\cos(\epsilon)$ can be ignored, because the cosine of these angles is then approximately one.

The weighting factors in the step 109 are dependent on the cone angle $\lambda$ and the fan angle $\epsilon$. The weighting factors are thus the same for all locations x in the examination zone which are traversed by the same ray, meaning that for these locations the weighting factors have to be calculated only once. In comparison with the known weighting by the weighting factor $1/|x-y(s)|$ of the equation (1), the foregoing leads to a substantial reduction of the required amount of calculation work.

Prior to the back projection rebinning of the measuring values can be performed in the step 111. As a result of the rebinning operation the measuring values are resorted and re-interpolated as if they had been measured by means of a different radiation source (an elongate radiation source which is arranged on a part of a helix and is capable of emitting each time mutually parallel fan beams) and by means of a different detector (a flat, rectangular "virtual" detector containing the axis of rotation 14).

Figure 8:
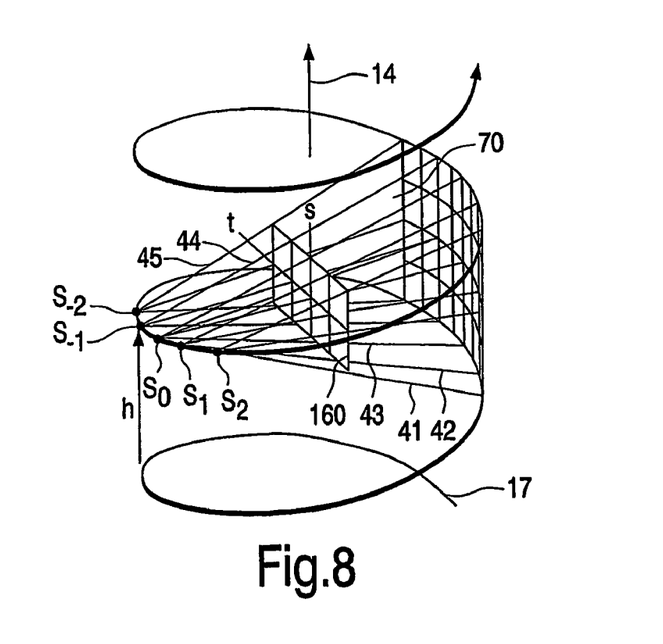
FIG. 8 shows the fan beams formed by rebinning in parallel planes.

This will be described in detail with reference to FIG. 8. Therein, the reference numeral 17 denotes the helical trajectory wherefrom the radiation source irradiates the examination zone. The reference numeral 43 denotes a fan-shaped radiation beam which emanates from the radiation source position $S_0$ and whose rays propagate in a plane containing the axis of rotation 14. The conical radiation beam emitted by the radiation source in the position $S_0$ can be assumed to consist of a plurality of flat fan beams which are situated in planes which are parallel to the axis of rotation 14 and intersect in the radiation source position $S_0$. FIG. 8 shows only a single one of these fan beams, that is, the fan beam 43.

Moreover, FIG. 8 shows further fan beams 41, 42 and 44, 45 which extend parallel to the fan beam 43 and are situated in planes which are parallel to one another and to the axis of rotation 14. The associated radiation source positions $S_{-2}$, $S_{-1}$ and $S_1$, $S_2$ are occupied by the radiation source S before and after having reached the radiation source position $S_0$, respectively. All rays in the fan beams 41 to 45 have the same projection angle.

The fan beams 41 to 45 define a radiation beam 70 having a tent-like shape. For each group of fan beams there is defined a rectangular, virtual detector 160 which is situated in a plane which contains the axis of rotation 14 and is oriented perpendicularly to the parallel fan beams of a group. The corner points of the virtual detector 160 constitute the puncture points of the rays, incident on the oppositely situated helical segment from the outer radiation source positions, through this plane. For the fan beam 70 in FIG. 8 these are the points of intersection of the fan beams 41 and 45 with the helix. On the rectangular detector 160 detector there are defined elements which are arranged in a cartesian fashion, that is, in rows and columns, on which the measuring values are re-interpolated.

The measuring values obtained after the rebinning are subsequently used for the reconstruction of the absorption distribution in the examination zone by a back projection which is in this embodiment in conformity with the equation (13).

In the step 113 a voxel V(x,y,z) is determined within a selectable (x,y,z) zone (field of view or FOV). Subsequently, in the step 115 a projection angle is selected within the range $[\phi_0, \phi_0+\pi]$ is selected, where $\phi_0$ is the angle at which the voxel V(x,y,z) enters the radiation beam. In the step 117 it is checked whether a ray of the projection extends through the center of the voxel V(x,y,z). If no ray of the projection passes through the center of the voxel, the associated value must be determined by interpolation of the measuring values of neighboring rays. The measuring value that can be associated with the ray passing through the voxel, or the measuring value obtained by interpolation, is accumulated on the voxel V(x,y,z) in the step 119. In the step 121 it is checked whether all projections with the projection angles $\phi_0$ to $\phi0+\pi$ have been taken into account. If this is not the case, the flow chart branches to the step 115. Otherwise, it is checked in the step 123 whether all voxels V(x,y,z) in the FOV have been dealt with. If this is not the case, the procedure continues with the step 113. However, when all voxels V(x,y,z) in the FOV have been dealt with, the absorption has been determined in the entire FOV and the reconstruction method is terminated (step 125).

LIST OF REFERENCES

1 gantry
2, 5 motor
3 collimator arrangement
4 conical radiation beam
7 control unit
10 image processing computer
11 monitor
13 examination zone
14 axis of rotation
16 detector unit
17 helix
31 PI line
35 object point
41 . . . 45 fan-shaped radiation beam
51 K plane
53 K line
160 virtual detector
S radiation source
$S_{-2} \ldots S_2$ radiation source positions.

The invention claimed is:

1. A computed tomography method which comprises the steps of:
   generating, using a radiation source, a conical radiation beam which traverses an examination zone or an object present therein,
   generating a relative motion of the radiation source about the examination zone, which relative motion comprises a rotation about an axis of rotation and a displacement parallel to the axis of rotation and is shaped as a helix, acquiring measuring values which are dependent on the intensity of the radiation beam that traverses the examination zone and is incident on a detector unit during the relative motions, and reconstructing a CT image of the examination zone from the measuring values, in which reconstruction of an exact 3D back projection comprising the following steps is carried out:

determining the partial derivative of measuring values of parallel rays with different radiation source positions in conformity with the angular position of the radiation source, performing a weighted integration of the partial derivative of the measuring values along K lines, multiplying the integrated partial derivative of the measuring values by a first weighting factor which corresponds to the cosine of the cone angle of the ray associated with the measuring values and by a second weighting factor which corresponds to the reciprocal value of the cosine of a fan angle of the beam associated with the measuring values, and reconstructing the absorption of each object point by back projection of the weighted, integrated partial derivative of the measuring values.

2. The computed tomography method as claimed in claim 1, in which in the reconstruction step further includes rebinning of the weighted, integrated partial derivative of the measuring values is performed prior to the back projection so as to form a number of groups, each group comprising a plurality of planes which extend parallel to one another and to the axis of rotation and in which a respective fan beam is situated.

3. A computer-readable medium encoded with a computer program for a control unit for controlling a radiation source, a diaphragm arrangement, a detector unit, a drive arrangement and a reconstruction unit of a computer tomograph so as to execute the steps disclosed in claim 1.

4. The system of claim 1, further including multiplying the integrated partial derivative of the measuring values by a first weighting factor which corresponds to the cosine of the cone angle of the ray associated with the measuring values, a second weighting factor which corresponds to the reciprocal value of the cosine of a fan angle of the beam associated with the measuring values, and a third weighting factor which corresponds to an inverse of a radius of the helix.

5. A computed tomography method which comprises the steps of:

generating, using a radiation source, a conical radiation beam which traverses an examination zone or an object present therein;

generating a relative motion of the radiation source about the examination zone, which relative motion comprises a rotation about an axis of rotation and a displacement parallel to the axis of rotation and is shaped as a helix;

acquiring measuring values which are dependent on the intensity of the radiation beam that traverses the examination zone and is incident on a detector unit during the relative motions; and reconstructing a CT image of the examination zone from the measuring values, in which reconstruction of an exact 3D back projection comprising the following steps is carried out:

determining the partial derivative of measuring values of parallel rays with different radiation source positions in conformity with the angular position of the radiation source;

performing a weighted-integration of the partial derivative of the measuring values along K lines;

multiplying the integrated partial derivative of the measuring values by a first weighting factor which corresponds to the cosine of the cone angle of the ray associated with the measuring values and by a second weighting factor which corresponds to the reciprocal value of the cosine of a fan angle of the beam associated with the measuring values; and reconstructing the absorption of each object point by back projection of the weighted, integrated partial derivative of the measuring values, wherein the weighted-integration of the measuring values along the K lines comprises the following steps:

determining a K plane for each radiation source position and each location to be reconstructed in the examination zone, determining the K lines, wherein the K lines are lines of intersection between the K planes and a detector surface of the detector unit, multiplying the partial derivative of the measuring values on each K line by a weighting factor which corresponds to the reciprocal value of the sine of a K angle, and integrating the partial derivative of the measuring values along the K lines.

6. A computer tomograph, comprising:

a radiation source and a diaphragm arrangement which is situated between the examination zone and the radiation source in order to generate a radiation beam which traverses an examination zone or an object present therein, a detector unit which is coupled to the radiation source, a drive arrangement which serves to displace an object present in the examination zone and the radiation source relative to one another about an axis of rotation and/or parallel to the axis of rotation, a reconstruction unit configured to reconstruct the spatial distribution of the absorption within the examination zone from measuring values acquired by the detector unit, a control unit configured to control the radiation source, the detector unit, the drive arrangement and the reconstruction unit in conformity with the steps of, determining the partial derivative of measuring values of parallel rays with different radiation source positions in conformity with the angular position of the radiation source, performing a weighted-integration of the derived measuring values along K lines, multiplying the integrated, derived measuring values by a first weighting factor which corresponds to the cosine of the cone angle of the ray associated with the measuring values and by a second weighting factor which corresponds to the reciprocal value of the cosine of a fan angle of the beam associated with the measuring values, and reconstructing the absorption of each object point by back projection of the weighted, integrated partial derivative of the measuring values.

7. A method, comprising:

producing measuring values indicative of radiation that traverses an examination zone and is detected by a radiation sensitive detector;

reconstructing the measuring values as a function of corresponding projection angles and weighting factors dependent on the location of the measuring value on the detector to generate an image indicative of the examination zone;

determining a partial derivative of the measuring values;
performing a weighted-integration of the partial derivative; and
reconstructing the integrated partial derivative to generate the image.

8. The method of claim 7, wherein a projection angle is the angle enclosed by a PI line of an object point projected in a plane perpendicular to an axis of rotation.

9. The method of claim 7, wherein the partial derivative is integrated along K lines.

10. The method of claim 7, wherein performing the weighted-integrating the partial derivative of the measuring values, includes:
determining a K plane for each radiation source position and each location to be reconstructed in the examination zone;
determining K lines, wherein K lines include lines of intersection between the K planes and a detector surface of the radiation sensitive detector;
multiplying the partial derivative of the measuring values on each K line by a weighting factor that corresponds to a reciprocal value of a sine of a K angle; and
integrating the partial derivative of the measuring values along the K lines.

11. The method of claim 7, further including, prior to the reconstruction step, multiplying the integrated partial derivative by the same weighting factor.

12. The method of claim 7, further including, prior to the reconstruction step:
multiplying the integrated partial derivative of the measuring values by the cosine of a cone angle of the radiation beam; and
dividing the integrated partial derivative of the measuring values by the cosine of a fan angle of the radiation beam.

13. The method of claim 7, wherein reconstructing the measuring values includes reconstructing the measuring values as a function of the following:

$$-\frac{1}{2\pi^2}\int_0^\pi d\varphi \frac{\cos\lambda}{R\cos\varepsilon} p(y(s(\varphi)), \Phi(s(\varphi), x)),$$

wherein, $p(y(s(\phi)),\Phi(s(\phi),x))$ denotes a weighted integration of a partial derivative of the measuring values, $$\frac{\cos\lambda}{R\cos\varepsilon}$$

denotes a weighting factor, $$\int_0^\pi d\varphi$$

denotes an integration over the projection angles $\phi$, $\lambda$ denotes a cone angle of the radiation, $\varepsilon$ denotes a fan angle of the radiation, R denotes a radius of a helical trajectory, x denotes a location in the examination zone, $s(\phi)$ denotes a parameter that is a function of $\phi$, y(s) denotes a function that indicates a radiation source position along the helical trajectory and is dependent upon a parameters, and $\Phi$ denotes a unity factor which points from the radiation source position y(s) in the direction of x.

14. The method of claim 7, wherein reconstructing the measuring values includes reconstructing the measuring values as a function of the following:

$$-\frac{1}{2\pi^2}\int_0^\pi d\varphi p(y(s(\varphi)), \Phi(s(\varphi), x)),$$

wherein, $p(y(s(\phi)),\Phi(s(\phi),x))$ denotes a weighted integration of a partial derivative of the measuring values, $$\int_0^\pi d\varphi$$

denotes an integration over the projection angles $\phi$, $\lambda$ denotes a cone angle of the radiation, $\varepsilon$ denotes a fan angle of the radiation, R denotes a radius of a helical trajectory, x denotes a location in the examination zone, $s(\phi)$ denotes a parameter that is a function of $\phi$, y(s) denotes a function that indicates a radiation source position along the helical trajectory and is dependent upon a parameter s, and $\Phi$ denotes a unity factor which points from the radiation source position y(s) in the direction of x.

15. A system, comprising:
a detector that detects radiation from a conical radiation beam traversing an examination zone and that generates measuring values indicative of the detected radiation; and
a reconstructor that integrates the measuring values over projection angles corresponding to angles enclosed by a PI line of an object point projected in a plane perpendicular to an axis of rotation;
wherein the measuring values are multiplied by a weighting factor dependent on the location of the measuring value on the detector, wherein the reconstructor determines the partial derivative of the measuring values, performs a weighted integration partial derivative, and integrates the weighted integration of the partial derivative of the measuring values.

16. The system of claim 15, wherein the weighted integration, includes:
determining a K plane for each radiation source position and each location to be reconstructed in the examination zone;
determining lines of intersection between the K planes and a detector surface of the detector, wherein the lines of intersection are K lines;
multiplying the partial derivative of the measuring values on each line of intersection by the weighting factor that corresponds to a reciprocal value of a sine of a K angle; and
integrating the partial derivative of the measuring values along the lines of intersection.

* * * * *